United States Patent [19]

DeNicola

[11] 4,160,325
[45] Jul. 10, 1979

[54] EXTENSOMETER

[75] Inventor: Joseph P. DeNicola, Hingham, Mass.

[73] Assignee: Instron Corporation, Canton, Mass.

[21] Appl. No.: 848,584

[22] Filed: Nov. 4, 1977

[51] Int. Cl.² .............................................. G01B 7/16
[52] U.S. Cl. .............................. 33/148 D; 33/DIG. 13
[58] Field of Search ..................... 33/148 D, DIG. 13; 73/88.5 SD, 99, 88 R, 89

[56] References Cited

U.S. PATENT DOCUMENTS

| | | | |
|---|---|---|---|
| 3,614,834 | 10/1971 | Holt et al. | 33/148 D |
| 3,620,071 | 11/1971 | Kelly et al. | 73/99 |
| 3,789,508 | 2/1974 | Meline | 33/148 D |

FOREIGN PATENT DOCUMENTS 534959  12/1956  Canada ................................. 33/148 D

*Primary Examiner*—Richard E. Aegerter
*Assistant Examiner*—Willis Little

[57] ABSTRACT

An extensometer capable of simultaneous measurement of axial strain and torsional deflection of a specimen subjected to axial or torsional load. A pair of gauge members define reference plane surfaces, one extending parallel and another extending perpendicular to the test axis. For each reference plane surface there is a follower capable of sensing only the component of relative displacement that lies in the direction normal to the reference plane surface. The sensed values of these followers represent relative axial and torsional displacement of the gauge members. The followers of the embodiment comprise cantilevers extending from ends fixed on one gauge member to ends biased against and freely riding upon the respective reference plane surfaces on the other gauge member. A calibration stand is also shown, comprising a two-part dummy specimen, the parts aligned to define a test axis. One dummy part, which is mounted for rotation on the axis and fixed against axial displacement along the axis, has a torque arm which a micrometer displaces to rotate the dummy part for calibration of the torsional sensing system of the extensometer. The second dummy part, which is fixed against rotation about the axis, is moved along the axis by a second micrometer for calibration of the axial strain sensing system of the extensometer. The parallelogram linkage of the embodiment employs resilient flexures. Clamps join the two gauge members when not in use.

11 Claims, 9 Drawing Figures

EXTENSOMETER

BACKGROUND OF THE INVENTION

This invention relates to extensometers for measuring axial strain and torsional deflection of a test specimen when it is subjected to load.

It is well known to be desirable to obtain both axial strain and torsional deflection readings simultaneously. Both types of strain occur even when it is sought to apply stress in only one direction. For instance, when a rod of solid material is tested for its elongation properties, the torsional deflection that accompanies axial elongation should also be measured in order to evaluate the specimen fully. Known practical techniques for determining the axial and torsional values, however, have interfered with each other and have prevented simultaneously accurate measurement. A principal object of this invention is to provide a practical device for overcoming this problem, and to enable the simultaneous measurement even when a specimen is subjected to chosen combinations of axial and torsional loading.

SUMMARY OF THE INVENTION

According to the invention a pair of gauge members for attachment to axially spaced apart points along the specimen, provide at least two reference plane surfaces, each fixed relative to a gauge member. One of these reference surfaces extends perpendicular and another extends parallel to the test axis. The position of each reference surface is detected by a follower on the other gauge member capable of sensing only the component of change of the relative position of this reference surface that lies in the direction normal to the plane of that surface. The sensed values produced by these followers then represent respectively the relative axial and torsional displacement of the gauge members.

In preferred embodiments each follower is a mechanical device having a contact point that rides freely upon the reference plane surface during change in position of the surface parallel to its own plane. Preferably this mechanical device comprises a spring cantilever extending from an end fixed on one gauge member to an end biased against the respective plane reference surface on the other gauge member. In preferred embodiments the cantilever comprises a sheet-form spring member, the plane of which lies generally parallel to the respective reference plane. A strain gauge is fixed to this cantilever element at the inflection point one-third of the distance from the fixed end of the cantilever, to avoid bending effects that may occur due to friction when the cantilever slides upon the reference plane. Preferably two strain gauges are employed, one one each face of a cantilever element and preferably pairs of symmetrically disposed reference planes are provided engaged by similar pairs of cantilever followers. The four strain gauges that are then associated with each reference direction are preferably connected in a resistance-comparing bridge to provide the desired reading.

In the illustrated embodiment the required reference plane and cantilever mountings are provided by a pair of interfiting elements each of which has integral posts which locate the respective reference planes and cantilevers.

A calibration stand is also provided according to the invention which restricts the ends of a dummy, two-part specimen from respective axial and rotational displacement while providing displacement in the free direction by micrometers.

Other objects and features of the invention will be understood from the following description of a preferred embodiment taken in conjunction with the drawings wherein:

BRIEF DESCRIPTION OF THE DRAWINGS

FIG. 5 is a diagrammatic view taken on line 5—5 of FIG. 2 illustrating relative torsional movement of the two sections of the extensometer during test, while;

DESCRIPTION OF THE PREFERRED EMBODIMENT

Figure 1:
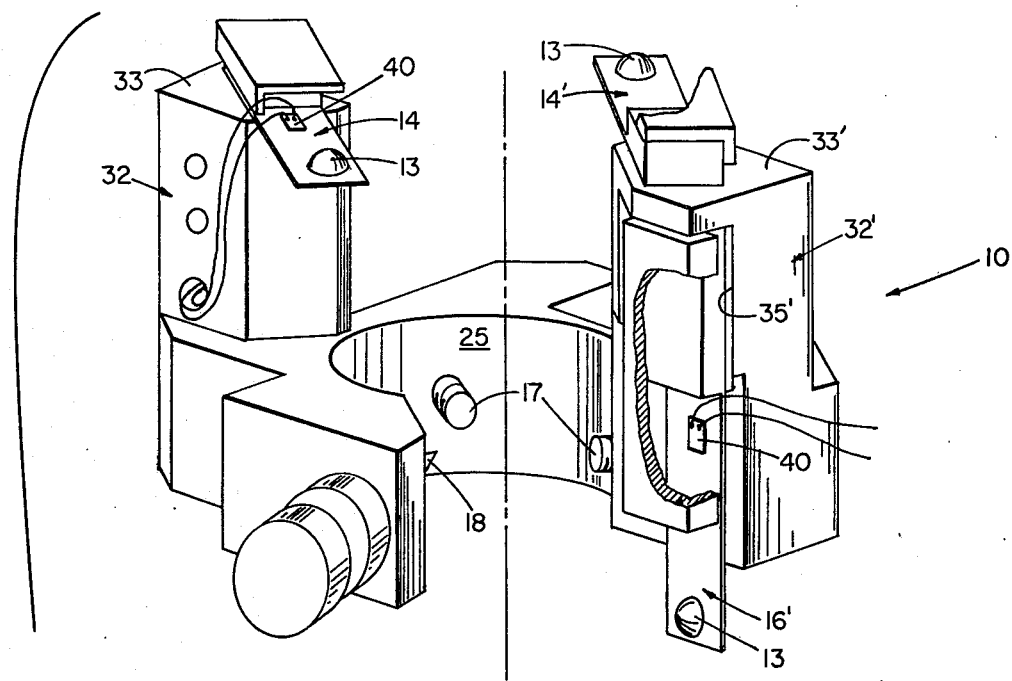
FIG. 1 is an exploded perspective view of a preferred embodiment of the extensometer of the invention.
Figure 1:
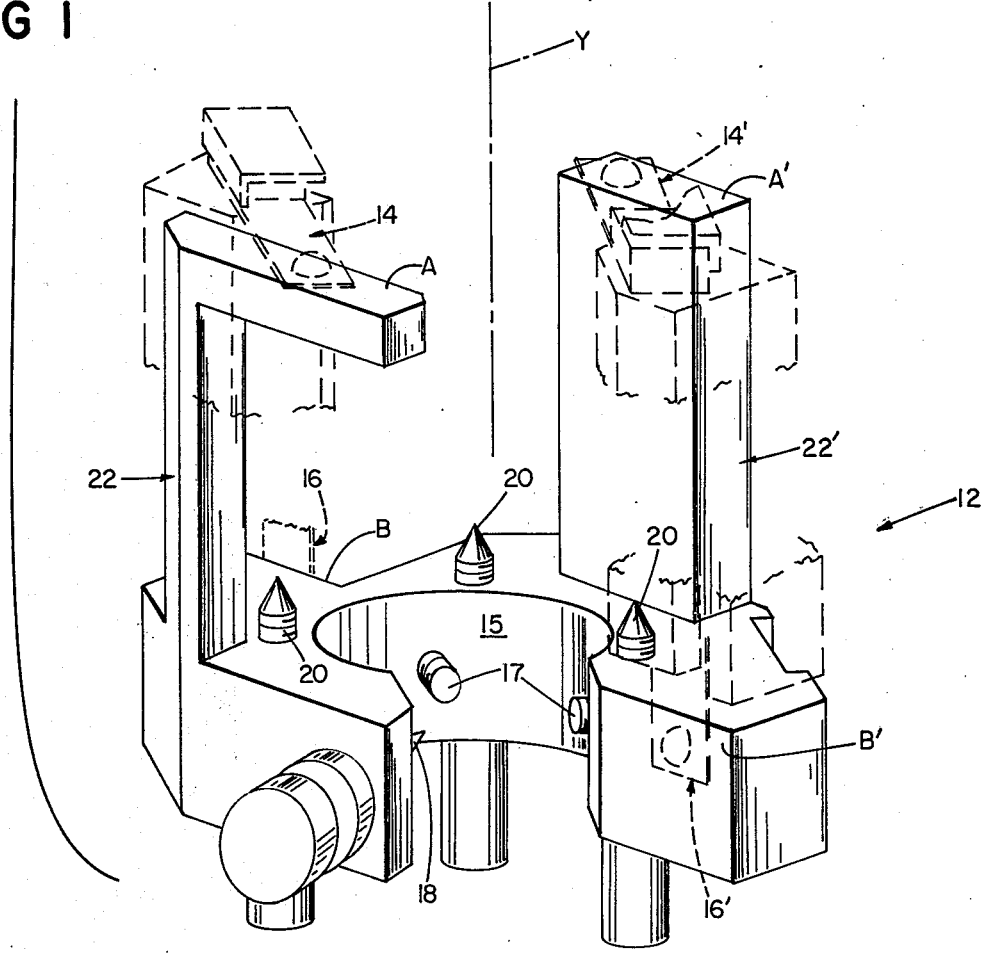

Referring to the exploded view of FIG. 1 this preferred embodiment comprises upper and lower gauge members 10, 12. The lower gauge member defines a pair of reference plane surfaces A and A' perpendicular to axis Y and a pair of reference plane surfaces B and B' parallel to axis Y. The upper gauge member 10 carries cantilever followers 14, 14' and 16, 16' which engage those reference plane surfaces.

In detail the lower gauge member 12 comprises a clamping ring 15 which has a pair of specimen centering screws 17 spaced 120° about the test axis Y and a clamping screw 18 which engages the opposite side of the specimen and presses it against the centering screws. Three equally, acurately spaced gauge-length positioning screws 20 are threaded axially through the clamping ring 15 for engagement with predetermined points on the upper gauge member 10 for setting its axial as well as its rotational position. The lower gauge member also includes a pair of posts 22 and 22' integral with and rising upwardly from the clamping ring 15, from diametrically spaced apart positions. These posts terminate at ends which define the reference plane surfaces A and A', lying perpendicular to the test axis Y. Side surfaces of lower clamping ring 12 itself define reference plane surfaces B and B' which lie parallel to the test axis Y.

The upper gauge member 10 similarly comprises a clamping ring 25 provided with centering screws 17 and clamping screw 18. The upper gauge member also includes a pair of posts 32 and 32' extending upwardly to define mounting surfaces for the cantilever elements. For this purpose the upper ends of the posts 32 and 32' define plane surfaces 33 and 33' lying perpendicular to the test axis Y, upon which are mounted the cantilever elements 14, 14' for detecting axial deflection. Sides of the posts 32 and 32' also define plane surfaces, 35 and 35', lying parallel to the test axis Y, upon which are mounted the cantilever elements 16, 16' for detecting torsional deflection. Suitable protective shields are shown extending over most of the length of the cantilevers.

Figure 3:
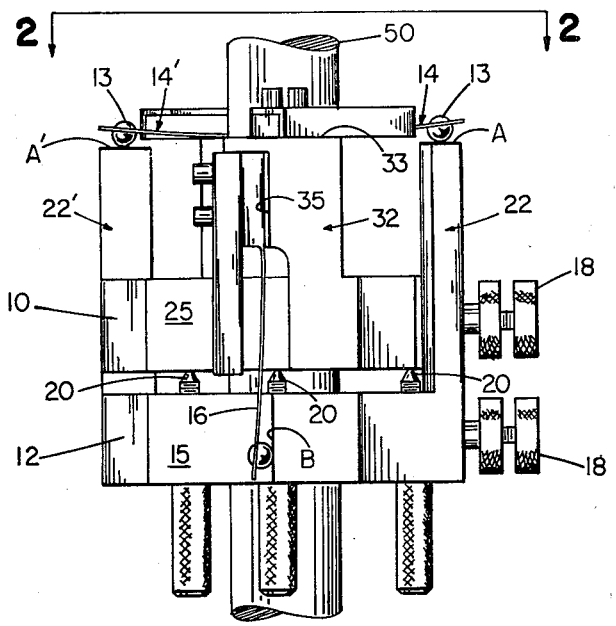
FIG. 3 is a side view taken on line 3—3 of FIG. 2.
Figure 2:
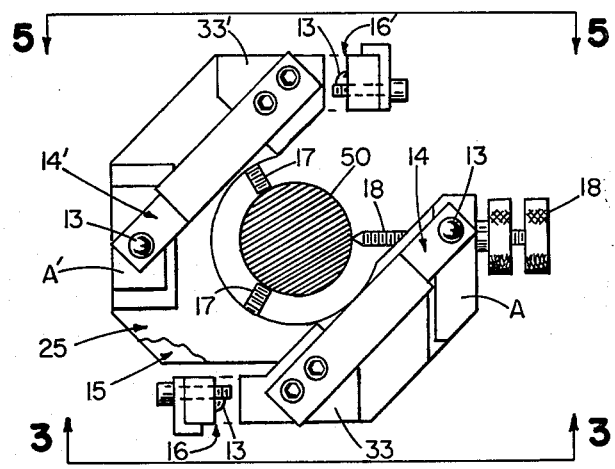
FIG. 2 is an end view of the extensometer of FIG. 1 applied to a test specimen.
Figure 4:
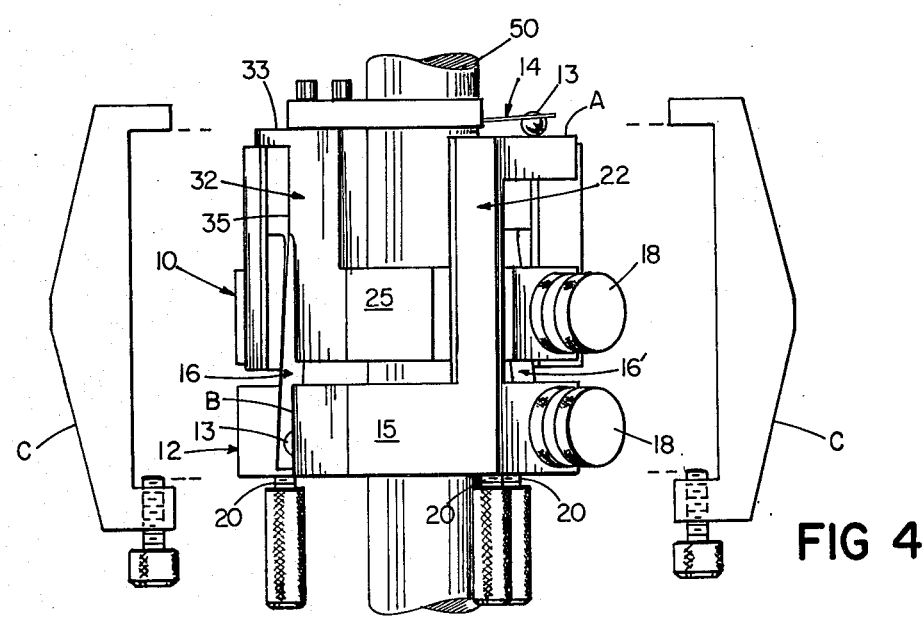
FIG. 4 is a similar side view taken from a position rotated from the position of FIG. 3 and showing auxiliary clamps.

In FIGS. 2–4 it is seen that the cantilever elements 14, 14′ have their fixed ends secured to the surfaces 33 and 33′ of the posts and the cantilevers extend horizontally to engage the reference plane surfaces A and A′ in a spring biased fashion. Thus the ends of the cantilevers can follow the axial movement of reference planes A and A′ (see FIG. 6) to sense axial strain of the specimens.

The pair of side-surfaces 35 and 35′ for mounting the axially extending cantilever elements 16, 16′ similarly extend to engage and follow the axial reference plane surfaces B and B′ (see FIG. 5) to sense torsional deflection of the specimen.

For the purpose of ensuring free riding of the ends of the cantilevers on the reference planes A, A′ and B, B′, the cantilevers terminate with polished ball surfaces 13 and the reference plane surfaces are hardened and provided with an antifriction surface. This is accomplished by anodizing the appropriate surfaces of the gauge member, which is aluminum, to a hardness of 60 Rockwell, followed by grinding to a surface finish of 6 micro inch, and then providing a polytetrafluoroethylene antifriction coating.

The cantilevers themselves are comprised of machined aluminum with an integral mounting base, with a width considerably greater than thickness. The width, lying parallel to the respective reference plane, serves to resist sideward deflection of the cantilever during translation of the reference surface parallel to its plane. The thinner dimension lies generally normal to the reference plane, permitting deflection with movements of the reference plane in the direction of its normal.

For sensing the deflection of the cantilevers, strain gauges 40 are provided, one on each face of each cantilever, the four strain gauges for each axis of movement being connected in a typical Wheatstone bridge, by which deflection can be measured.

In the free sliding movement of a cantilever relative to its reference plane, the slight inherent drag when in the direction tending to compress or stretch the cantilever along its length may impose a slight S-shaped curveform distortion to the cantilever. Even this is prevented from affecting the reading by placement of the strain gauges at a distance of one-third the length L of the cantilever from its fixed end, corresponding to the inflection point at which any curve deflection of the cantilever passes through zero. This is shown diagrammatically in FIG. 5.

In operation, the extensometer is assembled and then mounted on test specimen 50, as shown in FIGS. 2 through 4. Gauge-length positioning screws 20, of predetermined fixed lengths, are first adjusted to their extended position (FIG. 3). Then upper gauge member 10 is rotated until indentations in the under surface of its clamping ring engage upon the pointed ends of the extended screws 20. Both the angular position of the screws 20 and the angular position of the corresponding indentations have a predetermined position relative to the cantilever and reference surface pairs 16-B and 16′-B′, so that matching the screws 20 to the indentations biases each of these cantilevers against its reference surface to a predetermined mid-range position. The predetermined length of the screws 20 has the same effect on the cantilever and reference surface pairs 14-B and 14′-B′. With these adjustments made, C clamps, shown in FIG. 4, are applied to jig the upper and lower gauge members together, and the assembled extensometer is slipped over the test specimen 50 to the position shown in FIGS. 2 and 3. The clamping screws 18 for the upper and lower gauge members are tightened to lock the specimen in place against the centering screws 17 (FIG. 2). Thereupon the C clamps are removed and the gauge-length positioning screws 20 are backed off to the position of FIG. 4, thereby decoupling the upper and lower gauge members, permitting them to be relatively closed or opened apart axially and rotated in either direction about the test axis Y, during application of the test load.

Figure 5:
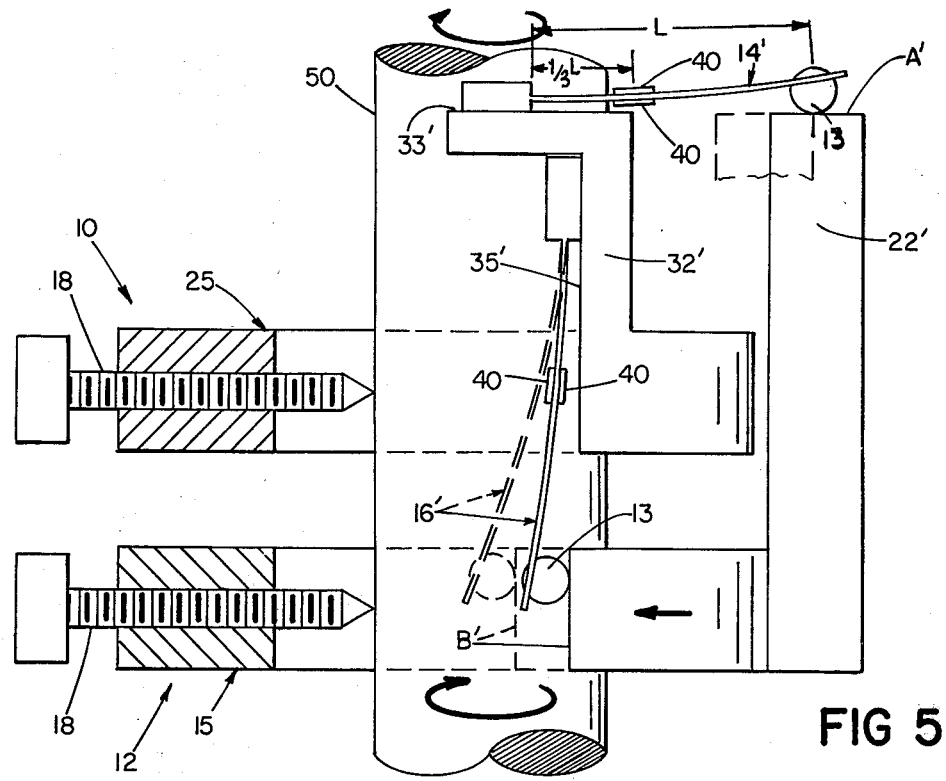
Figure 6:
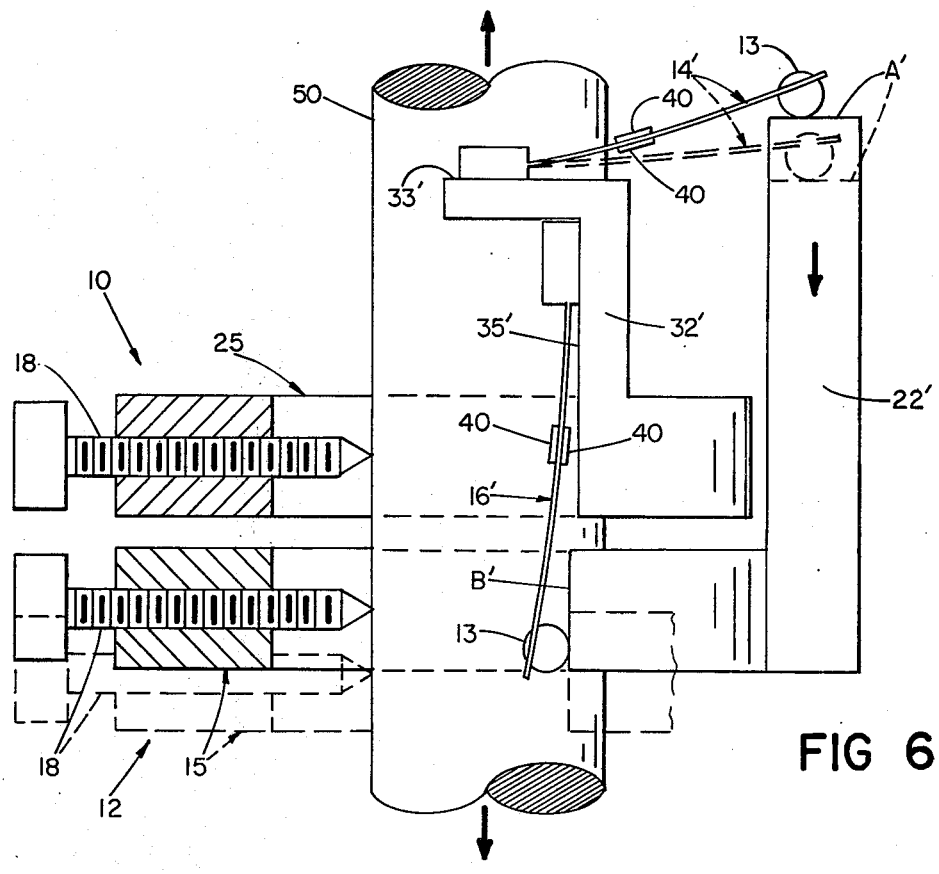
FIG. 6 is a similar view illustrating relative axial movement during test.

The immunity of the cantilevers during test to any but the orthogonal motions that have been described is diagrammatically illustrated in FIGS. 5 and 6. In FIG. 5, it is seen that pure rotation of the gauge members 10, 12 relative to one another, translates the reference surface B′, thus stressing cantilever 16′, and its strain gauges, thus to cause a torsional reading. Meanwhile, as shown in FIG. 5 reference surface A′ merely slides under the ball 13, with no change in the curvature of the associated cantilever, so there is no change in the stress of the strain gauges which read axial displacement. On the other hand, as illustrated in FIG. 6, pure relative axial displacement of the two gauge members produces change in the bend of cantilever 14′ to read axial strain, without affecting the torsional readings. Combinations of the two types of displacement result in accurate readings of the torsional and axial components, independent of each other.

Such decoupling of axial strain and torsional deflection permits accurate determination of any torsional delfection of a specimen that may occur under a pure axial load, and vice versa. It also permits accurate sensing of both axial and torsional effects produced by programmed combinations of torsional and axial stress applied to the test specimen.

For ease of manipulation, the C clamps are also applied when removing the extensometer from the test specimen.

Figure 7:
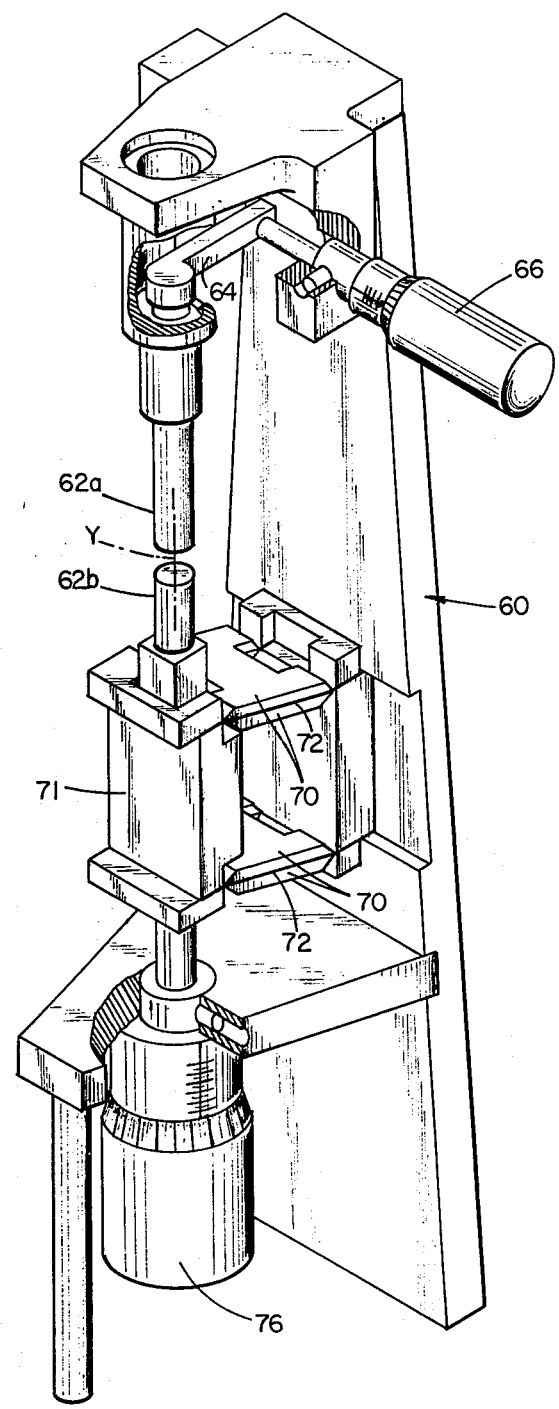
FIG. 7 is a perspective view of a preferred embodiment of the calibration stand of the invention.
Figure 8:
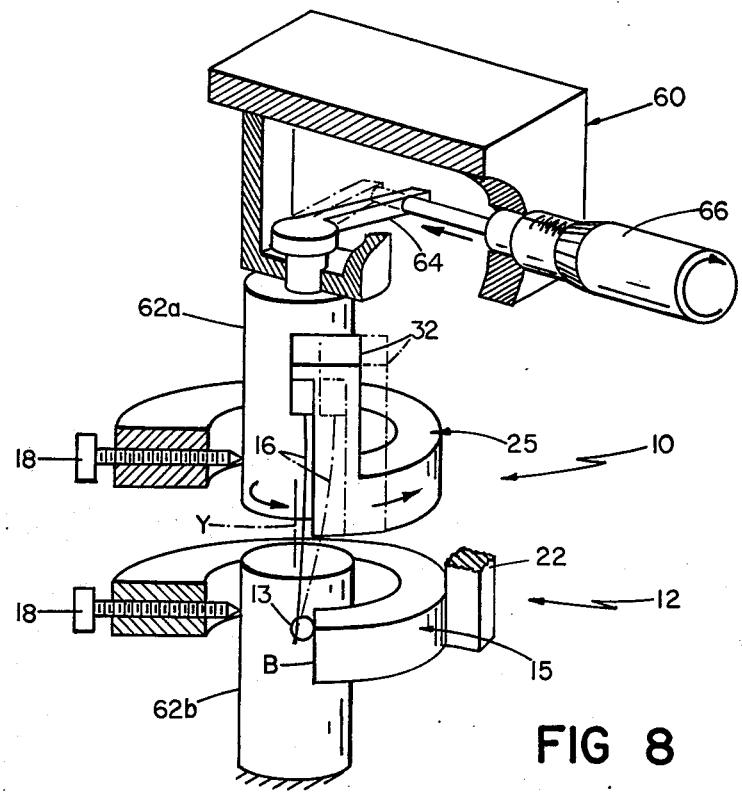
FIGS. 8 and 9 are diagrammatic views of the calibration stand of FIG. 7 being employed with the extensometer of FIG. 1, FIG. 8 illustrating calibration of the torsional and FIG. 9 illustrating the calibration of the axial sensing system.
Figure 9:
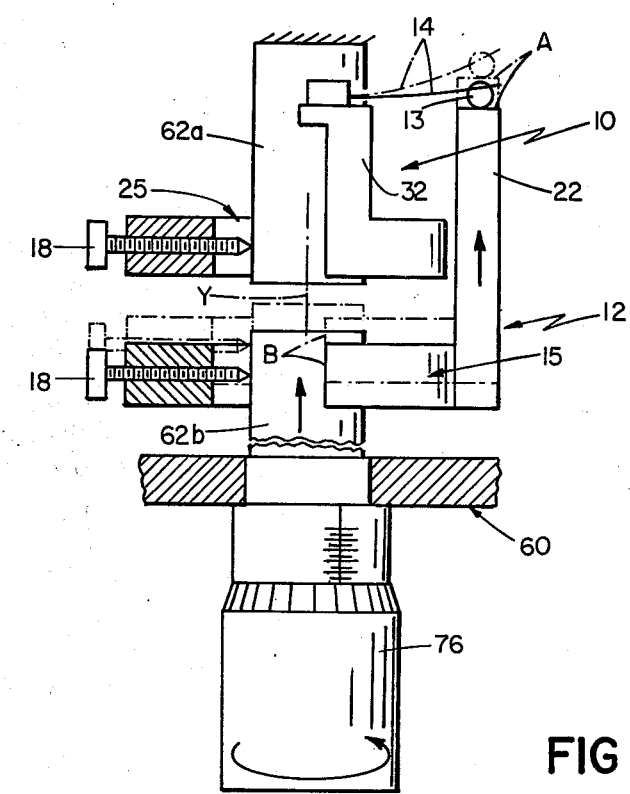

Referring to FIGS. 7, 8 and 9 for calibrating, a calibration stand 60 is provided in which a dummy test specimen comprising two independent parts 62a, 62b is provided. The top part 62a is to be clamped by the top gauge member 10. It is mounted for free rotation on the test axis Y, and constrained against axial movement of suitable thrust bearings. It is provided with a torque arm 64 to which a micrometer 66 applies tangential defection, thus to calibrate the torsional detection system. During such calibration the lower dummy test part 62b is constrained against rotation by a parallelogram linkage. This is formed by thin sheet metal flexures 72, each captured between a pair of rigid parallel plates 70 engaging its faces. The ends of the flexures are fixed respectively to the fixed part of the stand and to an axial plate 71. The resulting parallelogram linkage is rigid in the torsional direction about axis Y and permits only axial movement of the lower half of the dummy, along axis Y. Thus it is assured that all torsional deflection is dependent upon adjustment of the torque arm of the micrometer 66, associated with the first part of the dummy specimen.

For calibration of the axial deflection system, axial micrometer 76 is operated, by which the lower part 62b of the dummy specimen is moved an axially known distance, the upper part 62b being constrained by the previously mentioned thrust bearings.

For effective operation, torque arm 64 is spring biased rotationally against micrometer 66, and similarly the parallelogram linkage is biased axially against micrometer 76, in this case by deflection of the spring metal flexures from their unstressed position. Also the micrometers act upon the respective elements of the dummy specimen through ball bearings positioned in each case at the end of the micrometer.

What is claimed is:

1. An extensometer for simultaneous separate measurement of each of axial strain and torsional strain of a specimen with its axis along a test axis, which comprises
   a first gauge member,
      said gauge member including a clamping ring for clamping said first gauge member to said specimen at a first location along said axis,
   a second gauge member,
      said second gauge member including a second clamping ring for clamping said second gauge member to said specimen at a second location along said axis and axially spaced therealong from said first location,
   a first guide means,
   a second guide means,
   a first follower means, and
   a second follower means,
      said first follower means being guided by said first guide means,
         said first guide means being a planar surface parallel to said axis, and
         said first guide means being fixedly carried by one of said first gauge member and said second gauge member,
      said first follower means being carried by the other of said gauge members,
      said first follower means carrying sensing means for sensing deflection of said first follower means by said first guide means,
      said second follower means being guided by said second guide means,
         said second guide means being a planar surface perpendicular to said axis and
         said second guide means being fixedly carried by one of said gauge members,
      said second follower means being carried by the other of said gauge members,
      said second follower means carrying sensing means for sensing deflection of said second follower means by said second guide means,
   whereby said first guide means and first follower means produce a pure torsional strain readout and said second guide means and said second follower means provide a pure axial strain readout.

2. The extensometer of claim 1 in which each of said follower means comprises a cantilever beam with an end slidably movable along the associated guide means cooperating therewith.

3. The extensometer of claim 2 wherein said cantilever beam comprises a spring member which is thin in a direction perpendicular to said associated guide means and is wider in a direction parallel to said associated guide means.

4. The extensometer of claim 3 in which each said sensing means comprises a strain gauge and in which each said strain gauge is mounted one third the length of the cantilever beam from the fixed end thereof.

5. The extensometer of claim 1 wherein a said gauge member includes an integral, axially extending post, an end surface of said post defining a said second guide means.

6. The extensometer of claim 1 in which an external side surface of said clamp ring provides a said first guide means.

7. The extensometer of claim 1 which includes two said first guide means, two said first follower means, two said second guide means, and two said second follower means.

8. The extensometer of claim 7 in which all of said guide means are carried by one of said gauge members and all of said follower means are carried with the other of said gauge members.

9. The extensometer of claim 7 in which one of said first guide means is on the opposite side of said test axis from the other said first guide means and one said second guide means is on the opposite side of said test axis from the other of said second guide means.

10. The extensometer of claim 2 in which two strain gauges are carried on opposite sides thereof by each said follower means.

11. The extensometer of claim 1 wherein one of said gauge members comprises an array of axially extendable alignment elements, engageable upon predetermined points on the opposite gauge member, said alignment elements when engaged upon said points defining simultaneously correct axial and circumferential positions of said guide means and respective follower means, to place said followers in mid range of their travel for commencement of a test.

* * * * *